United States Patent
Delorme et al.

(10) Patent No.: US 12,270,045 B2
(45) Date of Patent: Apr. 8, 2025

(54) METHOD FOR PREPARING AN IRRADIATED PLATELET LYSATE

(71) Applicant: MACO PHARMA, Mouvaux (FR)

(72) Inventors: Bruno Delorme, Marcq-en-Baroeul (FR); Sabrina Viau, Wasquehal (FR)

(73) Assignee: Maco Pharma, Mouvaux (FR)

( * ) Notice: Subject to any disclaimer, the term of this patent is extended or adjusted under 35 U.S.C. 154(b) by 1211 days.

(21) Appl. No.: 16/969,600

(22) PCT Filed: Feb. 12, 2019

(86) PCT No.: PCT/EP2019/053472
§ 371 (c)(1),
(2) Date: Aug. 13, 2020

(87) PCT Pub. No.: WO2019/158540
PCT Pub. Date: Aug. 22, 2019

(65) Prior Publication Data
US 2021/0032590 A1    Feb. 4, 2021

(30) Foreign Application Priority Data
Feb. 15, 2018 (FR) ..................................... 1851307

(51) Int. Cl.
| C12N 5/00 | (2006.01) |
| A61K 41/17 | (2020.01) |
| C12N 5/078 | (2010.01) |
| C12N 9/64 | (2006.01) |

(52) U.S. Cl.
CPC ............ *C12N 5/0018* (2013.01); *A61K 41/17* (2020.01); *C12N 5/0644* (2013.01); *C12N 9/6437* (2013.01); *C12N 9/644* (2013.01); *C12N 9/6443* (2013.01); *C12N 2529/10* (2013.01)

(58) Field of Classification Search
None
See application file for complete search history.

(56) References Cited

U.S. PATENT DOCUMENTS

| 2012/0156306 A1 | 6/2012 | Weissman et al. | |
| 2018/0289744 A1* | 10/2018 | Delorme | C12N 5/0662 |

FOREIGN PATENT DOCUMENTS

| WO | 2008034476 A1 | 3/2008 | |
| WO | 2008034803 A1 | 3/2008 | |
| WO | 20100033605 A1 | 3/2010 | |
| WO | 2013003356 A1 | 1/2013 | |
| WO | 2013042095 A1 | 3/2013 | |
| WO | 2014076200 A1 | 5/2014 | |
| WO | 2016193591 A1 | 12/2016 | |
| WO | WO 16/193591 * | 12/2016 | ............. C12N 5/078 |
| WO | 20170162830 A1 | 9/2017 | |

OTHER PUBLICATIONS

International Search Report issued in corresponding application No. PCT/EP2019/053472 dated May 29, 2019.
Viau et al, Pathogen reduction through additive-free short-wave UV light irradiation retains the optimal efficacy of human platelet lystate for the expansion of human bone marrow mesenchymal stem cells, PLoS One, vol. 12, No. 8, Aug. 1, 2017 (Aug. 1, 2017), p. e0181406, DOI:10.1371/journal.pone0181406 XP055495757.
Castglia et al. Inactivated human platelet lysate with psoralen: a new perspective for mesenchymal stromal cell production in Good Manufacturing Practice conditions. Cytotherapy 16.6 (2014): 750-763.
Laner-Plamberger et al, Mechanical fibrinogendepletion supports heparin-free mesenchymal stem cell propagation in human platelet lysate, J Transl Med (2015) 13:354: 2-10.
Pons et al, Human platelet lysate as validated replacement for animal serum to assess chemosensitivity, ALTEX-Alternatives to animal experimentation (2018) 277-288.
Fekete et al, Platelet lysate from whole blood derived pooled platelet concentrates and apheresis-derived platelet concentrates for the isolation and expansion of human bone marrow mesenchymal stromal cells: production process, content and identification of active components, Cytotherapy, 2012; 14: 540-554.
Burnouf T., et al.: Human platelet lysate: replacing foetal bovine serum as a gold standard for human cell propagation? Biomaterials 2016; 76:371-387.

* cited by examiner

*Primary Examiner* — Allison M Fox
(74) *Attorney, Agent, or Firm* — Harris Beach Murtha Cullina PLLC

(57) ABSTRACT

The invention relates to a method for preparing an irradiated platelet lysate, comprising the steps of providing a starting platelet lysate having platelet factors including growth factors and plasma proteins including coagulation factors and proteins other than the coagulation factors. Double irradiation of the starting platelet lysate, using UVC radiation and ionizing radiation. The double irradiation with UVC radiation and ionizing radiation being arranged to retain at least 75% of the total protein concentration of the starting platelet lysate, while reducing, by at least 40%, the concentration of at least one of the coagulation factors including fibrinogen, factor II, factor VII, factor IX, factor X and factor XI of the starting platelet lysate.

19 Claims, 6 Drawing Sheets

METHOD FOR PREPARING AN IRRADIATED PLATELET LYSATE

CROSS-REFERENCE TO RELATED APPLICATIONS

This application claims the benefit of International application number PCT/EP2019/053472, filed Feb. 12, 2019 and French application number 1851307, filed Feb. 15, 2018 the entire contents of which are incorporated herein by reference.

TECHNICAL FIELD

The invention relates to a method for preparing an irradiated platelet lysate as well as an irradiated platelet lysate obtained by such a method and a method for culturing cells using such an irradiated platelet lysate.

BACKGROUND

The invention applies to the field of blood platelet derived products, and in particular to the field of cell culture for cultivating cells for therapeutic use, more particularly mesenchymal stem cells.

To cultivate animal cells in vitro, conventionally basal mediums of the RPMI (Roswell Park Memorial Institute), MEM (Modified Eagle Medium) or DMEM (Dulbecco Modified Eagle Medium) type are used comprising substantially mineral salts, glucose, amino acids, vitamins and nitrogenous bases. These basal mediums are generally extemporaneously supplemented with antibiotics in order to prevent bacterial contamination, L-glutamine—an unstable amino acid—, and between 1.5 and 10% foetal calf serum as a nutritive supplement.

In order to use more effective products and in order to avoid the use of xenogeneic products in cell cultures for therapeutic use, it has been proposed to replace the foetal calf serum with human platelet lysate. The latter has in particular the advantage of comprising a substantial quantity of growth factors such as for example TGF-beta1 (Transforming Growth Factor-beta1), EGF (Epidermal Growth Factor), PDGF-AB (Platelet-Derived Growth Factor-AB), PDGF-BB (Platelet-Derived Growth Factor-BB), IGF-1 (Insulin-like Growth Factor-1), VEGF (Vascular Endothelial Growth Factor) FGF-2 (Fibroblast Growth Factor 2), also called bFGF (Basic Fibroblast Growth Factor).

Thus, the following human or non-human animal cells were cultivated in the presence of platelet lysate: keratinocytes, renal epithelial cells, leukemic cell lines or solid tumour derived leukemic cells, as well as human primary cells such as adipocytes, stem cells of the amniotic fluid, bone marrow stem cells, chondrocytes, corneal cells, endothelial cells, keratinocytes, mesenchymal stem cells, monocytes and osteoblasts (Pons, Miriam, et al. "Human platelet lysate as validated replacement for animal serum to assess chemosensitivity." ALTEX-Alternatives to animal experimentation (2018).

The platelet lysate is typically prepared from a suspension of platelets in plasma or in a mixture of plasma and an additive solution for platelets, that is subjected to one or more freezing/thawing cycles to release the growth factors contained in the platelets by cell lysis.

A disadvantage with such a platelet lysate is that it contains fibrinogen, coming from the plasma, in a quantity varying from about 0.5 to 3 mg/ml, in such a way that the adding of an anticoagulant to the basal medium is required in order to avoid a coagulation of the basal medium (Burnouf T, Strunk D, Koh M B, et al.: Human platelet lysate: replacing foetal bovine serum as a gold standard for human cell propagation? Biomaterials 2016; 76:371-387).

The most widely used anticoagulant is heparin. But the commercially available heparins are generally of porcine origin, in such a way that the culture medium, although devoid of foetal calf serum, still comprises a xenogeneic product.

Furthermore, at certain concentrations, heparin has a negative effect on cell proliferation (Viau, Sabrina, et al. "Pathogen reduction through additive-free short-wave UV light irradiation retains the optimal efficacy of human platelet lysate for the expansion of human bone marrow mesenchymal stem cells." PloS one 12.8 (2017): e0181406).

Several strategies have been proposed to eliminate the coagulation power of a platelet lysate:

A first method is described in document WO 2013/003356, which consists of adding calcium chloride to the platelet lysate, inducing the conversion of the fibrinogen into fibrin and the formation of a clot. The clot is then eliminated by centrifugation in order to obtain a lysate comprising less than 0.05 mg/ml of fibrinogen. This method however generates a loss in growth factors that might be trapped in the clot.

An indirect method consists of eliminating the plasma that contains the fibrinogen from the starting platelet suspension, for example by carrying out several platelet washing cycles before preparing the platelet lysate. This strategy is for example described in document WO 2008/034803 and in document US 2012/0156306. The elimination of the plasma however generates in fact the elimination of other plasma proteins such as albumin, required for cell proliferation.

In document WO 2017/162830, it is proposed to eliminate the plasma from the starting platelet suspensions then to heat the platelet lysate between 55 and 65° C. for 20 to 40 minutes, so as to obtain a quantity of fibrinogen less than 0.3 mg/ml. However, this method also reduces the quantity of the other proteins present in the platelet lysate by at least 70%, which is not desirable for a use in cell culture.

Laner-Plamberger et al. propose an original method consisting of adding the non-defibrinogenated platelet lysate to the basal medium in order to form a fibrin gel, then to destroy and eliminate this gel by vigorous agitation and centrifugation. The basal medium supplemented with platelet lysate thus obtained is devoid of fibrinogen, but still contains the other plasma proteins (J Transl Med (2015) 13:354). This method is however complex to set up in the context of a standardised and quality-controlled industrial production of platelet lysates.

In document WO 2016/193591, the platelet lysate is subjected to an irradiation with ionising radiation in order to be sterilised. According to the dose of irradiation used, the irradiated platelet lysate can comprise less than 0.4 mg/ml of fibrinogen. According to the example described, a platelet lysate was prepared from platelet concentrates comprising platelets suspended in 30% plasma and 70% preservation solution, then irradiated at a dose of 35 or 45 kGy. When the platelet lysate is added in a quantity of 8% to the basal medium, the basal medium does not coagulate.

Additional irradiation tests with gamma radiation carried out by the applicant have shown that the coagulation power of the platelet lysate depended not only on the dose of irradiation used, but also on the quantity of proteins in the platelet lysate and on the quantity of platelet lysate added to the basal medium.

Thus, a platelet lysate prepared from platelet concentrates comprising platelets suspended in 30% plasma, comprising between 20 and 30 g/l of total proteins, and radiated at about 35 kGy according to the method described in document WO 2016/193591, coagulates at 15% and more in a basal medium MEM devoid of heparin. A platelet lysate prepared from platelet concentrates comprising platelets suspended in 100% plasma, comprising between 60 and 80 g/l of total proteins, and irradiated at 35 kGy according to the method described in document WO 2016/193591, coagulates at 5% in a basal medium MEM devoid of heparin.

To reduce the coagulation power of a platelet lysate, the applicant has considered increasing the dose of irradiation used up to 75 kGy in order to obtain a sterilised platelet lysate that does not coagulate, even at a strong concentration in the basal medium. But at a very strong dose of irradiation with gamma radiation, the plasma proteins of interest for cell growth are degraded.

There remains therefore a need to obtain a platelet lysate with a reduced coagulation power in the presence of calcium, even when the platelet lysate is added at a high concentration in a basal medium comprising calcium, while still preserving the plasma proteins.

Furthermore, document WO 2013/042095 and the article by S. Castiglia (Castiglia, Sara, et al. "Inactivated human platelet lysate with psoralen: a new perspective for mesenchymal stromal cell production in Good Manufacturing Practice conditions." Cytotherapy 16.6 (2014): 750-763) disclose a platelet lysate obtained from buffy coat derived platelet concentrates that have been subjected to a viral inactivation by an ultraviolet radiation of the UVA type in the presence of psoralen, a DNA-intercalating chemical agent. This technique of viral inactivation however has the disadvantage of having to use a chemical agent that must then be eliminated from the treated product.

Another method of obtaining a platelet lysate devoid of pathogens is described in the article by S. Viau (Viau, Sabrina, et al. "Pathogen reduction through additive-free short-wave UV light irradiation retains the optimal efficacy of human platelet lysate for the expansion of human bone marrow mesenchymal stem cells." PloS one 12.8 (2017): e0181406). In this article, a platelet lysate is obtained from platelet concentrates which were subjected to a viral inactivation by UVC radiation, in the absence of chemical agent.

In these latter documents, the platelet lysate prepared from virus-inactivated platelet concentrates remain coagulable.

The invention proposes a method for preparing a platelet lysate with a reduced coagulation power in the presence of calcium, while still retaining the plasma proteins required in particular for cell proliferation.

Thus, according to a first aspect, the invention proposes a method for preparing an irradiated platelet lysate comprising the following steps:
  providing a platelet lysate in order to obtain a starting platelet lysate, the starting platelet lysate comprising on the one hand platelet factors including growth factors and on the other hand plasma proteins including coagulation factors and proteins other than the coagulation factors,
  double irradiation of the starting platelet lysate, with UVC radiation having a wavelength comprised between 200 and 280 nm and with ionising radiation having a wavelength less than or equal to 100 nm, in order to obtain a platelet lysate irradiated with UVC radiation and with ionising radiation, the double irradiation with UVC radiation and with ionising radiation being arranged to retain at least 75% of the total protein concentration of the starting platelet lysate while reducing, by at least 40% the concentration of at least one of the coagulation factors including fibrinogen, factor II, factor VII, factor IX, factor X and factor XI of the starting platelet lysate.

According to a second aspect, the invention relates to the irradiated platelet lysate obtained by the method according to the first aspect of the invention.

According to a third aspect, the invention proposes a method for the culture of cells, particularly animal cells and more particularly mesenchymal stem cells, comprising the putting of the cells into contact with a nutritive composition comprising a basal medium and an irradiated platelet lysate according to the second aspect of the invention.

BRIEF DESCRIPTION OF THE DRAWINGS

Other objects and advantages shall appear in the following description.

DETAILED DESCRIPTION

Figure 1:
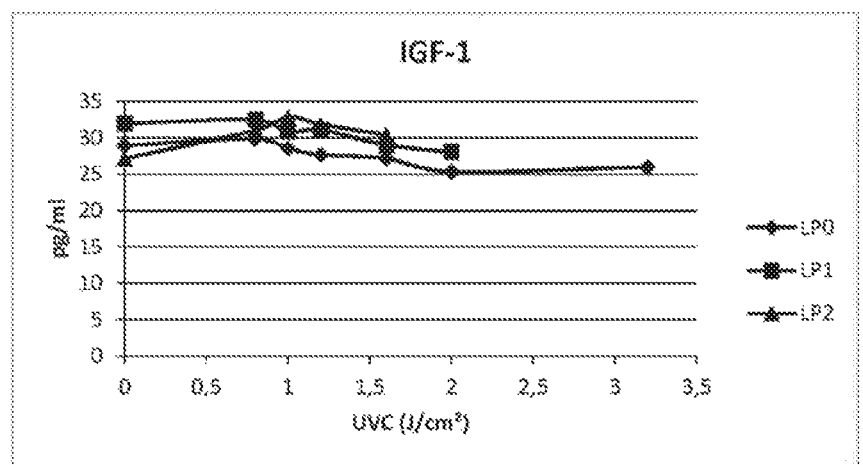
FIGS. 1 to 6 show, respectively, the concentrations in IGF-1, TGF-beta1, bFGF, PDGF-AB, EGF and VEGF factors in three batches of platelet lysate irradiated with UVC radiation, according to the dose of irradiation.
Figure 2:
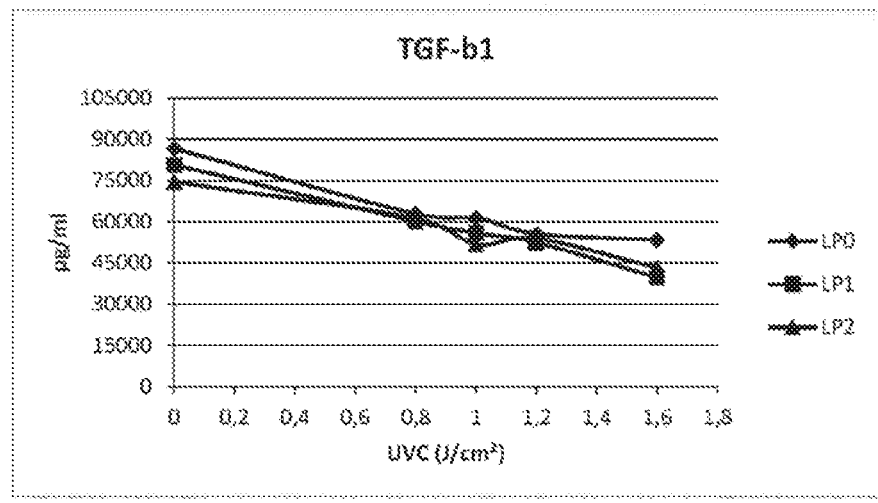
Figure 3:
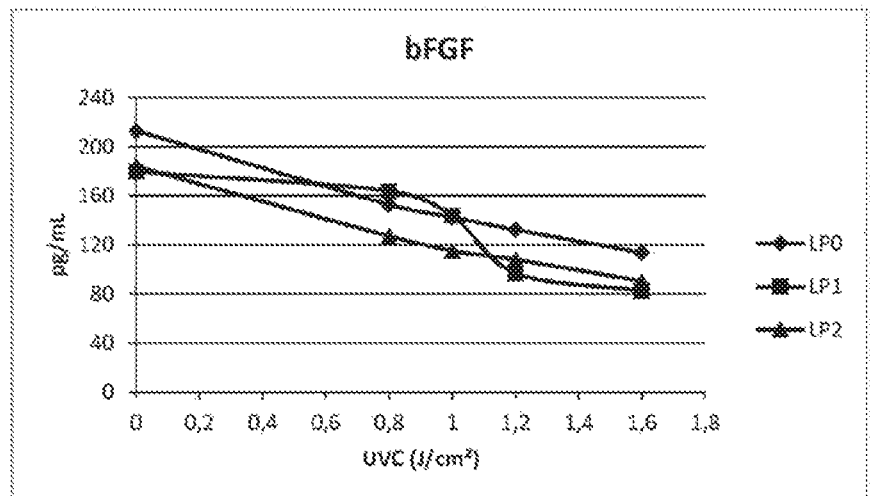

The invention relates to a method for preparing an irradiated platelet lysate for the purpose in particular of obtaining a platelet lysate having a reduced coagulation power.

"Platelet lysate" means the product of the lysis of platelets, i.e. the product obtained after the disintegration of the cell membrane of the platelets which leads to the release of molecules (growth factors, cytokines) normally contained inside platelets.

The lysis of the platelets is for example carried out by one or more freezing/thawing cycles, by the use of ultrasound or by a solvent/detergent treatment.

The method according to the invention comprises firstly a step consisting of providing a platelet lysate in order to obtain a starting platelet lysate, the starting platelet lysate comprising on the one hand platelet factors including growth factors and on the other hand plasma proteins including coagulation factors and proteins other than the coagulation factors.

The platelet lysate is produced from platelets in suspension in a liquid comprising plasma. Such a suspension of platelets is for example a platelet concentrate or a mixture of platelet concentrates, a buffy coat layer, or a mixture of buffy coat layers, a platelet-rich plasma or a mixture of platelet-rich plasmas.

More particularly, the platelet suspension is a platelet concentrate coming from apheresis or prepared from a blood donation or a mixture of platelet concentrates coming from aphaeresis or prepared from blood donations.

For example, the mixture comprises between 4 and 50 platelet concentrates, in particular between 5 and 30 platelet concentrates.

Preparing a platelet lysate from a mixture of several platelet concentrates, in particular more than four platelet concentrates, is advantageous because it makes it possible to standardise the platelet lysate, i.e. to homogenise the concentration of the various components thereof, in particular the concentration of growth factors (Viau S, Eap S, et al. A standardized and characterized clinical grade human platelet lysate for efficient expansion of human bone marrow mesenchymal stem cells. Cytotherapy. May 2017, Volume 19, Issue 5, Supplement, Page S195).

Indeed, the concentrations of growth factors of a platelet lysate depend on the initial platelet donor.

The platelet concentrates are either fresh, i.e. qualified to be transfused to a patient, or expired, i.e. stored for 5 days or more after the preparation thereof and no longer suitable to be transfused to a patient.

Such platelet concentrates comprise platelets in suspension in a liquid medium containing plasma.

For example, the liquid medium comprises only plasma. According to another example, the liquid medium further comprises a preservation solution of the platelets, such as the solution SSP+(Maco Pharma) or Intersol® (Fresenius Kabi).

In a particular example, the liquid medium comprises from 20% to 100%, in particular 30% plasma and from 0% to 80%, in particular 70% platelet preservation solution.

The lysis of a suspension of platelets comprising platelets in plasma provides a starting platelet lysate comprising on the one hand platelet factors normally contained inside platelets and on the other hand constituents of the plasma.

The plasma comprises water at 90%, salts such as sodium, chlorine and calcium, lipids such as triglycerides and cholesterol, hormones, vitamins such as vitamin B12 and vitamin D and proteins such as albumin, immunoglobulins, the coagulation factors such as fibrinogen, antithrombin III involved in the coagulation chain, globulins, interleukins and interferons.

Thus, the starting platelet lysate to which the method of the invention is applied comprises in particular on the one hand platelet factors including growth factors and on the other hand plasma proteins including coagulation factors and proteins other than the coagulation factors.

These growth factors are in particular TGF-beta1, EGF, PDGF-AB, IGF-1, VEGF and bFGF. Other growth factors that can be found in the platelet lysate are in particular CTGF (Connective Tissue Growth Factor) and SDF-1 alpha (Stromal Cell-Derived Factor-1 alpha). These growth factors are referred as endogenous.

"Endogenous substance" means any substance produced by the platelets or comprised in the starting platelet suspension used to prepare the platelet lysate, in opposition to an exogenous substance introduced into the platelet lysate or into the starting platelet suspension.

For example a platelet lysate produced from lysis by freezing/thawing of a platelet suspension comprises the following concentrations of growth factor:

TABLE 1

| bFGF | 110-180 pg/ml |
|------|---------------|
| PDGF-AB | 20,000-45,000 pg/ml |
| PDGF-BB | 12,000-15,000 pg/ml |
| IGF-1 | 25-150 pg/ml |
| VEGF | 500-1,000 pg/ml |
| EGF | 1,600-3,000 pg/ml |
| TGFbeta1 | 30,000-80,000 pg/ml |

The starting platelet lysate comprises on the other hand plasma proteins including coagulation factors and proteins other than the coagulation factors.

The coagulation factors are in particular fibrinogen, factor II, factor VII, factor IX, factor X and factor XI. Other coagulation factors are factor V and factor VIII.

The other proteins of the plasma other than the coagulation factors are in particular albumin and antithrombin III, a protein involved in the coagulation chain.

The total quantity proteins of the starting platelet lysate therefore depends on the percentage of plasma in the starting platelet suspension, before lysis of the platelets.

For example, a starting platelet lysate produced from lysis by freezing/thawing of platelet concentrates comprising platelets suspended in 100% plasma includes in particular the following components:

TABLE 2

| Total proteins (mg/ml) | 60-80 mg/ml |
|------|---------------|
| Fibrinogen (mg/ml) | 0.5-1.5 mg/ml |
| Vitamin B12 | 250-300 pg/ml |

In another example, a starting platelet lysate produced from lysis by freezing/thawing of platelet concentrates comprising platelets suspended in 30% plasma and 70% of a preservation solution of the platelets comprises in particular the following components:

TABLE 3

| Total proteins (mg/ml) | 20-30 mg/ml |
|------|---------------|
| Fibrinogen (mg/ml) | 0.45-0.5 mg/ml |
| Vitamin B12 | 150-170 pg/ml |

The step of providing a platelet lysate is to be understood as the making a platelet lysate available. That is to say the method of the invention is implemented on a platelet lysate produced beforehand by lysis of the platelets of a platelet suspension.

After the step of providing a starting platelet lysate, the method according to the invention comprises double irradiation of the starting platelet lysate with UVC radiation having a wavelength comprised between 200 and 280 nm and with ionising radiation having a wavelength less than or equal to 100 nm on the other hand, in order to obtain a platelet lysate irradiated with UVC radiation and with ionising radiation, the double irradiation with UVC radiation and with gamma radiation being arranged to retain at least 75% of the total protein concentration of the starting platelet lysate while reducing, by at least 40% the concentration of at least one of the coagulation factors including fibrinogen, factor II, factor VII, factor IX, factor X and factor XI of the starting platelet lysate.

The step of double irradiation is to be understood as a first irradiation followed by a second irradiation. In particular, the first irradiation is an irradiation with UVC radiation and the second irradiation is an irradiation with ionising radiation. Alternatively, the first irradiation is an irradiation with ionising radiation and the second irradiation is an irradiation with UVC radiation. The first and second irradiations are successive, i.e. carried out one after the other.

The step consisting of irradiating the platelet lysate with UVC radiation having a wavelength comprised between 200 and 280 nm in order to obtain a platelet lysate irradiated with UVC radiation is in particular arranged to retain at least 75% of the total protein concentration of the starting platelet lysate while reducing, by at least 20% the concentration of at least one of the coagulation factors including fibrinogen, factor II, factor VII, factor IX, factor X and factor XI of the starting platelet lysate.

"UVC radiation" refers to a non-ionising electromagnetic radiation, i.e. a radiation that is not able to cause the ionisation of atoms or of molecules. UVC radiation has a wavelength comprised between 200 and 280 nm, in particular 254 nm.

By retaining more than 75% of the total proteins of the starting platelet lysate, the platelet lysate irradiated with UVC radiation can be used as a supplement for basal medium for cell culture. In particular, the albumin which represents more than 50% of the proteins in the plasma and which is a particularly important nutrient in cell culture, is retained at at least 80% with respect to the starting platelet lysate.

In particular, at least 80%, and more particularly at least 90% of the total protein concentration in the platelet lysate irradiated with UVC radiation is retained with respect to the starting platelet lysate.

The platelet lysate irradiated with UVC radiation comprises a total protein concentration ranging from 20 to 80 mg/ml, according to the concentration of plasma of the starting platelet suspension.

For example, a platelet lysate produced from lysis by freezing/thawing of platelet concentrates comprising platelets suspended in 100% plasma then irradiated with UVC radiation comprises a total protein concentration ranging from about 55 mg/ml to about 80 mg/ml.

According to another example, a platelet lysate produced from lysis by freezing/thawing of platelet concentrates comprising platelets suspended in 30% plasma then irradiated with UVC radiation comprises a total protein concentration ranging from about 18 mg/ml to about 30 mg/ml.

In addition, by reducing by at least 20% the concentration of one of the coagulation factors including fibrinogen, factor II, factor VII, factor IX, factor X and factor XI, the coagulation power of the platelet lysate irradiated with UVC radiation is reduced.

That is to say a basal medium comprising calcium, for example about 0.2 g/l of calcium chloride will not coagulate in the presence of platelet lysate irradiated with UVC radiation or coagulate from a concentration of platelet lysate irradiated with UVC radiation in the basal medium higher than a starting platelet lysate from which the basal medium coagulates.

For example, the basal medium alphaMEM coagulates in the presence of 5% or more of starting platelet lysate, while this medium coagulates from 10% or more of platelet lysate irradiated with UVC radiation.

In particular, the platelet lysate irradiated with UVC radiation is added in a range from 2 to 25%, in particular in the range from 5 to 15%, and more particularly in the range from 8 to 10% in a basal medium.

The platelet lysate irradiated with UVC radiation having a reduced coagulation power, the use thereof as a basal medium supplement for cell culture is possible, in certain concentrations, without using any anticoagulant such as heparin.

In particular, the irradiation with UVC radiation is arranged to reduce, by at least 20% the concentration of each one of the coagulation factors including fibrinogen, factor II, factor VII, factor IX, factor X and factor XI of the starting platelet lysate.

For example, a platelet lysate produced from lysis by freezing/thawing of platelet concentrates comprising platelets suspended in 30% plasma then irradiated with UVC radiation comprises the following plasma constituents.

TABLE 4

| Total proteins (mg/ml) | 14-30 mg/ml |
|---|---|
| Fibrinogen (mg/ml) | <0.4 mg/ml |
| Vitamin B12 | 125-140 pg/ml |

In addition, the starting platelet lysate comprises in particular the TGF-beta1, EGF, PDGF-AB, IGF-1, VEGF and bFGF endogenous growth factors.

The irradiation with UVC radiation is in particular arranged to retain at least 80% of the concentration of one of the growth factors including IGF-1, PDGF-AB, EGF and VEGF of the starting platelet lysate, in particular in order to be able to use the irradiated platelet lysate as a basal medium supplement.

In particular, the irradiation using UVC radiation is arranged to retain at least 80% of the concentration of each one of the growth factors including IGF-1, PDGF-AB, EGF and VEGF, in particular in order to be able to use the irradiated platelet lysate as a basal medium supplement.

For example, a platelet lysate produced from lysis by freezing/thawing of platelet concentrates comprising platelets suspended in 30% plasma then irradiated with UVC radiation comprises the following growth factors.

TABLE 5

| bFGF | 88-140 pg/ml |
|---|---|
| PDGF-AB | 16,000-45,000 pg/ml |
| PDGF-BB | 6,400-12,000 pg/ml |
| IGF-1 | 20-120 pg/ml |
| VEGF | 400-900 pg/ml |
| EGF | 1,300-2,800 pg/ml |
| TGF-beta1 | 24,000-70,000 pg/ml |

The irradiation with UVC radiation is in particular arranged to retain at least 75%, particularly at least 80%, of the amplification factor of the mesenchymal stem cells cultivated for 7 days in a basal medium supplemented with starting platelet lysate.

According to a particular embodiment, the irradiation with UVC radiation is carried out at a dose comprised between 0.01 to 2 J/cm$^2$, particularly between 0.5 J/cm$^2$ and 1.5 J/cm$^2$, and more particularly at 1 J/cm$^2$.

A dose of UVC radiation less than 0.01 J/cm$^2$ is not sufficient to degrade the coagulation factors present in the starting platelet lysate. A dose of UVC radiation greater than 2 J/cm$^2$ damages the growth factors generating a substantial loss in cell proliferation.

In particular, the starting platelet lysate is irradiated with UVC radiation in the liquid state.

For example, the starting platelet lysate in the liquid state is contained in a UVC-permeable recipient, such as a UVC-permeable irradiation bag. A UVC-permeable irradiation bag is in particular made from a material that does not have an adsorption maximum in the range from 200 to 280 nm. The irradiation bag is in particular made from ethylene vinyl acetate or from polytetrafluoroethylene.

The irradiation bag containing the starting platelet lysate is then disposed in an UVC illumination device. The bag is stirred orbitally during the irradiation with UVC radiation, in such a way as to homogeneously irradiate all of the platelet lysate.

Alternatively, the irradiation with UVC radiation of the starting platelet lysate is carried out under a flow condition.

According to a particular embodiment, the method comprises, prior to the irradiation with UVC radiation, a step of filtering the starting platelet lysate through a filter with a porosity of 0.65 µm or less, particularly 0.45 µm or less.

This step of filtering makes it possible to eliminate any cellular debris coming from the step of lysing of the platelets and which could hinder the irradiation of the platelet lysate.

According to another particular embodiment, the method comprises, after the irradiation with UVC radiation, a step of sterilising filtration of the platelet lysate irradiated with UVC radiation through a filter with a porosity of 0.45 µm or less, particularly 0.22 µm or less.

This step of filtering through a sterilising filter makes it possible to retain bacteria having a size greater than 0.22 µm and, combined with the irradiation with UVC radiation, makes it possible to obtain a platelet lysate having a reduced risk of bacterial and viral contamination.

In order to further reduce the coagulation power of the platelet lysate irradiated with UVC radiation, the method according to the invention comprises a step of irradiating the platelet lysate with ionising radiation having a wavelength less than or equal to 100 nm, particularly less than 10 nm.

Ionising radiation having a wavelength less than or equal to 100 nm comprises X-UV rays having a wavelength ranging from 10 nm to 100 nm, X rays having a wavelength ranging from 10 µm to 10 nm and gamma rays having a wavelength less than 10 µm.

A method of irradiating a platelet lysate using ionising radiation is in particular described in patent application WO 2016/193591.

In such a method, prior to the step of irradiating with ionising radiation, the method comprises a step of freezing the platelet lysate in order to irradiate with ionising radiation the platelet lysate in the frozen state.

In particular, the freezing of the platelet lysate is carried out at a temperature comprised between −10° C. and −196° C., in particular about −20° C. or about −80° C.

Alternatively, the platelet lysate is irradiated with ionising radiation in a freeze-dried state.

For the irradiation with ionising radiation in a frozen state, the platelet lysate is contained in a recipient that resists freezing and in particular in a bag that resists freezing. The material that is resistant to freezing is in particular ethylene vinyl acetate, polyethylene or a fluoropolymer such as fluorinated ethylene-propylene.

According to a particularly advantageous embodiment, the irradiation with ionising radiation is carried out after the irradiation with UVC radiation, i.e. the irradiation with ionising radiation is carried out on the platelet lysate irradiated with UVC radiation.

More advantageously, the irradiation with ionising radiation is carried out after the irradiation with UVC radiation and after the sterilising filtration of the platelet lysate irradiated with UVC radiation, i.e. on the platelet lysate irradiated with UVC radiation then filtered in a sterile manner.

In this case, the step of irradiating with ionising radiation is carried out on the platelet lysate in its final conditioning, in particular in a storage bag. The storage bag is for example made from a material that resists freezing and the irradiation with ionising radiation such as ethylene vinyl acetate.

Alternatively, the irradiation with ionising radiation is carried out prior to the irradiation with UVC radiation on the starting platelet lysate.

According to an embodiment, the ionising radiation is a gamma radiation having a wavelength less than or equal to 10 µm.

Gamma radiation is an electromagnetic radiation comprised of high-energy photons, of about 1.6 MeV. It is for example emitted by a cobalt 60 source.

The irradiation with ionising radiation is arranged in such a way so as to retain, in the platelet lysate irradiated with ionising radiation, at least 80% of the concentration of at least one of the endogenous growth factors selected from the group comprising TGF-beta1, EGF, PDGF-AB, IGF-1 and VEGF of the platelet lysate before irradiation with ionising radiation.

In particular, the irradiation with gamma radiation is arranged in such a way so as to retain in the platelet lysate irradiated with ionising radiation, at least 80%, particularly at least 90%, and more particularly 95% of the concentration of each one of the TGF-beta1, EGF, PDGF-AB, IGF-1 and VEGF growth factors, of the platelet lysate before irradiation with ionising radiation.

For example, the irradiation with ionising radiation is an irradiation with gamma radiation carried out at an absorbed dose comprised in the range from 20 kGy to 75 kGy, in particular from 35 kGy to 55 kGy.

The absorbed dose is the quantity of energy communicated to the material by unit of mass.

For example, the irradiation is carried out during a duration comprised in the range from 600 seconds to 1,800 seconds, preferably from 900 seconds to 1,200 seconds, and more preferably for 1,075 seconds, with a source that has an activity of 1 Mci (3.7×1,019 Bq).

According to a method of the invention, the platelet lysate is subjected to a double irradiation with UVC radiation and with ionising radiation, i.e. a first irradiation with UVC radiation followed by a second irradiation with ionising radiation, or a first irradiation with ionising radiation followed by a second irradiation with UVC radiation.

Advantageously, the irradiation with ionising radiation and the irradiation with UVC radiation are arranged together in order to retain at least 75% of the total protein concentration of the starting platelet lysate.

Thus, the doubly irradiated platelet lysate retains its interest for a use in cell culture or other application for which the proteins have an interest.

The retaining of most of the proteins of interest, all of them or most of them, as well as the retaining of the biochemical factors (factors also important for cell growth) of a doubly irradiated lysate makes it possible to offset the partial loss in certain growth factors induced by each one of the two irradiations with UVC radiation and ionising radiation.

Furthermore, the irradiation with ionising radiation and the irradiation with UVC radiation are arranged together in such a way so as to reduce by at least 40% the concentration of at least one of the coagulation factors including factor II, factor VII, factor IX, factor X and factor XI of the starting platelet lysate.

In particular, the irradiation with ionising radiation and the irradiation with UVC radiation are arranged together in such a way as to reduce by at least 40% the concentration of each one of the coagulation factors including factor II, factor VII, factor IX and factor XI of the starting platelet lysate.

For example, a platelet lysate produced from lysis by freezing/thawing of platelet concentrates comprising platelets suspended in 30% plasma, irradiated with UVC radiation then irradiated with ionising radiation comprises the following components.

TABLE 6

| Total proteins (mg/ml) | 18-30 mg/ml |
| Fibrinogen (mg/ml) | <0.4 mg/ml |
| Vitamin B12 | 120-140 pg/ml |

Thus, the coagulation power of the doubly irradiated platelet lysate is substantially reduced, in such a way that it can be added at a high concentration, i.e. up to at least 20% to a basal medium containing calcium without coagulating, in the absence of anticoagulant such as heparin.

For example, the irradiation with UVC radiation is carried out at a dose comprised between 0.01 to 2 J/cm$^2$, particularly between 0.5 J/cm$^2$ and 1.5 J/cm$^2$, and more particularly at 1 J/cm$^2$, and the irradiation with ionising radiation is an irradiation with gamma radiation carried out at an absorbed dose comprised in the range from 20 kGy to 60 kGy, particularly from 35 kGy to 45 kGy.

As certain growth factors are not impacted at the same level by the irradiation with UVC radiation and by the irradiation with ionising radiation, it is possible to modulate the quantity of growth factors in a platelet lysate by modulating the respective parameters of each one of the two irradiations.

In addition, the irradiation with UVC radiation and the irradiation with gamma radiation having an antibacterial and antiviral effect, the method of the invention furthermore makes it possible to obtain a highly-secure product from a viral and/or bacterial standpoint.

According to an aspect, the invention relates to an irradiated platelet lysate obtained by the method according to the first aspect of the invention.

The platelet lysate prepared according to the method of preparing of the invention has a particular growth factor and protein profile.

In particular, the irradiation with UVC radiation impacts certain growth factors that are not impacted or less impacted by an irradiation with ionising radiation. These growth factors include in particular the EGF, TGF-beta1 and PDGF-BB factors.

For example, the platelet lysate irradiated with UVC radiation comprises a concentration of endogenous EGF growth factor less than 2,800 µg/ml, and/or a concentration of endogenous TGF-beta1 growth factor less than 70,000 µg/ml, in particular less than 40,000 ng/ml, and/or a concentration of endogenous PDGF-BB growth factor less than 12,000 µg/ml.

The same applies for vitamin B12 impacted by the UVC radiation but not by the ionising radiation.

For example, the platelet lysate irradiated with UVC radiation comprises a concentration of vitamin B12 reduced by 10 to 30% with respect to the starting platelet lysate. In particular, the concentration of vitamin B12 is comprised in the range from 125 to 140 µg/ml.

Certain growth factors or proteins are not or are hardly impacted by the irradiation with UVC radiation and by the irradiation with ionising radiation.

Thus, the platelet lysate irradiated with UVC radiation and ionising radiation comprises a concentration of PDGF-AB growth factor comprised in the range from 16,000 to 45,000 µg/ml.

Certain growth factors or proteins are not impacted by the irradiation with UVC radiation, but are impacted by the irradiation with ionising radiation.

For example, antithrombin III, a protein involved in the coagulation chain is only slightly impacted by the irradiation with UVC radiation, but is more substantially impacted by the ionising radiation.

Certain growth factors are impacted by both the irradiation with UVC radiation and by the irradiation with ionising radiation.

Thus, the platelet lysate irradiated with UVC radiation comprises a concentration of endogenous bFGF growth factor less than 140 µg/ml.

When the platelet lysate is in addition irradiated with ionising radiation, the concentration of endogenous bFGF growth factor is less than 90 µg/ml.

The platelet lysate irradiated with UVC radiation and using ionising radiation further comprises a concentration of fibrinogen less than 0.4 mg/ml.

The double irradiation with UVC radiation and ionising radiation does not have any notable impact on the total protein concentration of the platelet lysate.

Thus, the platelet lysate irradiated with UVC radiation and irradiated with ionising radiation comprises a total protein concentration comprised between 14 and 80 mg/ml, according to the starting quantity of plasma.

More particularly, the total protein concentration in a platelet lysate produced from lysis by freezing/thawing of platelet concentrates comprising platelets suspended in 100% plasma, irradiated with UVC radiation and with ionising radiation comprises a total protein concentration ranging from about 55 mg/ml to about 80 mg/ml.

The total protein concentration in a platelet lysate produced from lysis by freezing/thawing of platelet concentrates comprising platelets suspended in 30% plasma, irradiated with UVC radiation and with ionising radiation comprises a total protein concentration ranging from about 18 mg/ml to about 30 mg/ml.

According to a third aspect, the invention relates to a method for the culture of cells, particularly of animal cells, and more particularly mesenchymal stem cells, comprising the putting of the cells into contact with a nutritive composition comprising a basal medium and an irradiated platelet lysate according to the second aspect of the invention.

The method applies for example to the culture of human or non-human animal cells, such as keratinocytes, epithelial cells, leukemic cell lines or solid tumour derived leukemic cell lines, adipocytes, stem cells of the amniotic fluid, bone marrow stem cells, chondrocytes, corneal cells, endothelial cells, mesenchymal stem cells, monocytes, osteoblasts and natural killer cells.

The mesenchymal stem cells are for example human mesenchymal stem cells derived from bone marrow or umbilical cord blood.

According to a particular embodiment, the nutritive composition comprises from 2% to 25%, in particular from 5% to 15%, and more particularly from 8 to 10% of irradiated platelet lysate according to the invention.

In particular, the irradiated platelet lysate is added extemporaneously in a preliminary manner to the basal medium in such a way as to form the nutritive composition.

As the irradiated platelet lysate has a reduced coagulation power, it is not necessary to add to the nutritive composition an anticoagulant of the heparin type in order to prevent the coagulation thereof and maintain it in a liquid state.

Thus, according to an embodiment of the method for the culture of cells, particularly animal cells, the nutritive composition is in liquid form and is free of anticoagulant.

Example 1

Platelet Lysate Irradiated with UVC Radiation 1.1 Preparation of a Platelet Lysate A batch of platelet lysate is prepared as described hereinbelow.

Platelet concentrates (20 platelet concentrates) comprising 70% Intersol® preservation solution and 30% plasma were prepared from a mixture of five buffy coats and retained in storage bags.

The storage bags were frozen at −80° C. for a duration of about 24 hours before being thawed at 4° C. for about 24 hours.

The thawed storage bags are then centrifuged at a speed of 5,000 g for 10 minutes in such a way as to separate the supernatant comprising the platelet lysate from the sediment comprising the cellular debris.

The supernatant of each one of the storage bags is transferred into a mixture bag so as to obtain a mixture of platelet lysates (PL).

1.2 Irradiation with UVC

The mixture of platelet lysates is transferred, by volume of 500 ml, into irradiation bags. The air and all the bubbles are eliminated from the irradiation bags.

The irradiation bags are then irradiated with an UVC illumination device (Macotronic UV, Maco Pharma, France), at different doses (0-3.2 J/cm$^2$). The irradiation bags are stirred at a speed of 110 rpm.

After irradiation with UVC radiation, the contents of the irradiation bags are re-mixed in a transfer bag.

1.3 Dosages of Cytokines

The following tests, carried out on three batches (PL0, PL1, PL2), were carried out in order to characterise the platelet lysates irradiated at different UVC doses:

Dosages using ELISA kits of IGF-1 (ref. DG100/batch 341313) and of TGF-Beta1 (ref. DB100B/batch 340010),
Dosages using ELISA kits of bFGF (ref. DFB50/batch P104841), of PDGF-AB (ref. DHD00C/batch P101565), of EGF (ref. DEG00/batch 339998), and of VEGF (ref. DVE00/batch P100719)

The results, shown in FIG. 1, show that the concentration of IGF-1 in the platelet lysate is not impacted by the irradiation with UVC radiation.

Figure 4:
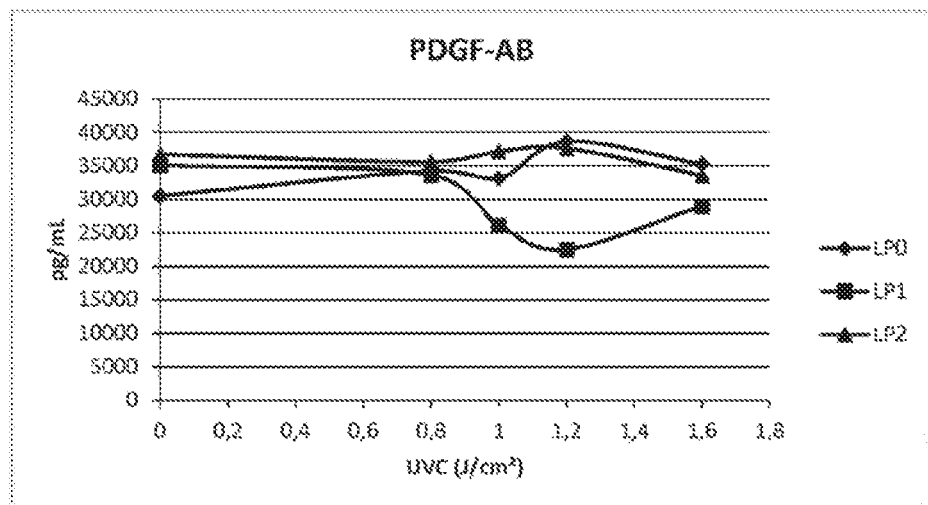
Figure 5:
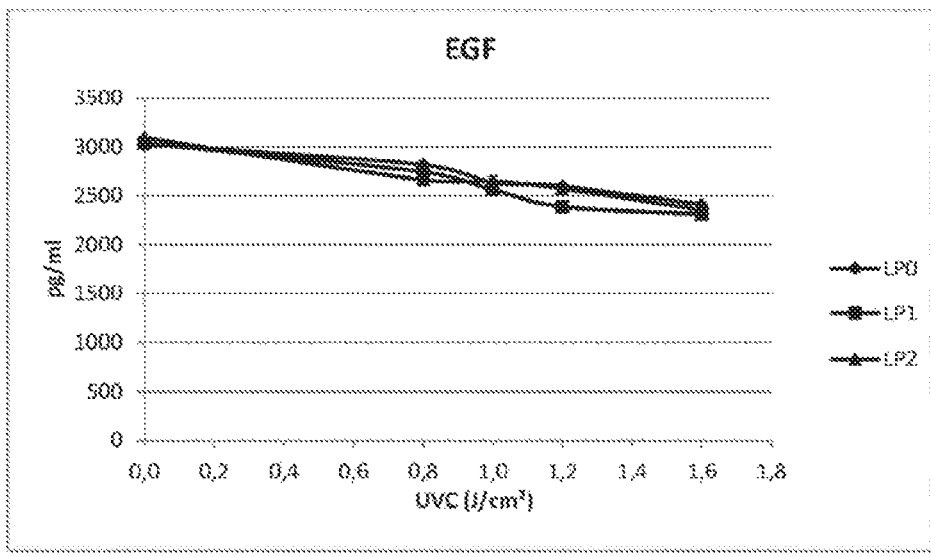
Figure 6:
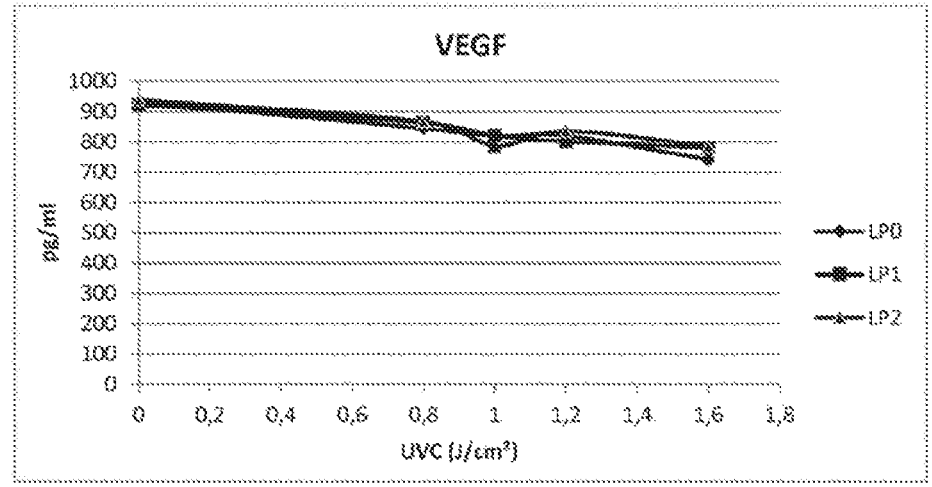
Figure 7:
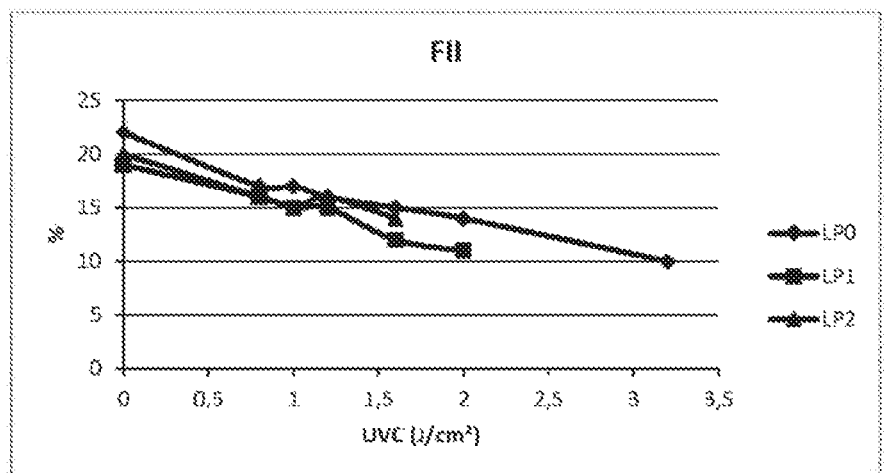
FIGS. 7 to 11 show, respectively, the concentrations of factor II, factor VII, factor IX, factor X and factor XI coagulation factors, expressed as a percentage with respect to a standard normal human plasma, in three batches of platelet lysate irradiated with UVC radiation, according to the dose of irradiation.
Figure 8:
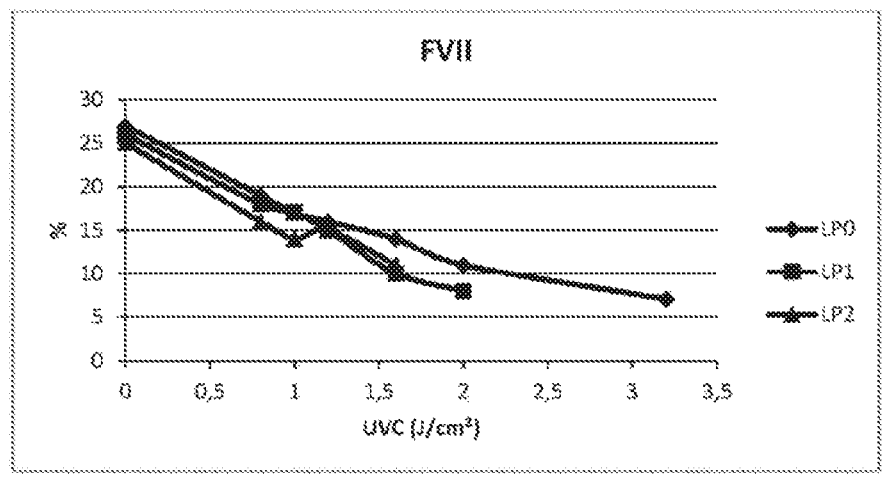
Figure 9:
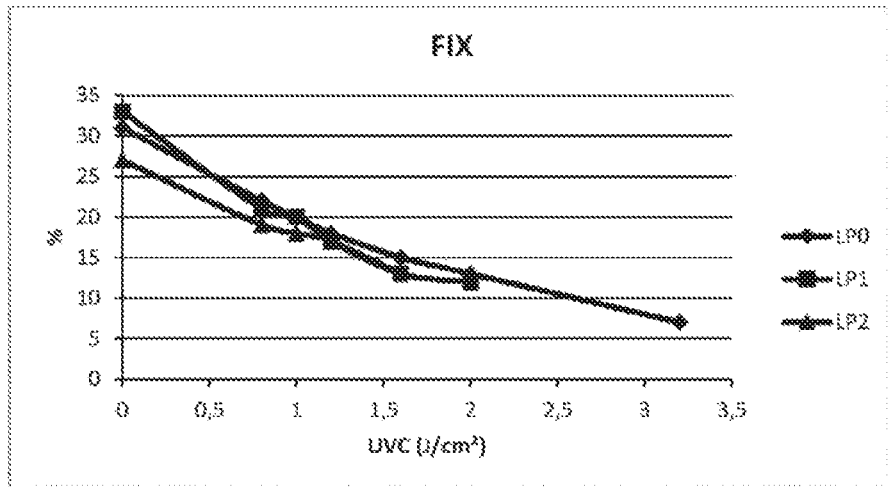
Figure 10:
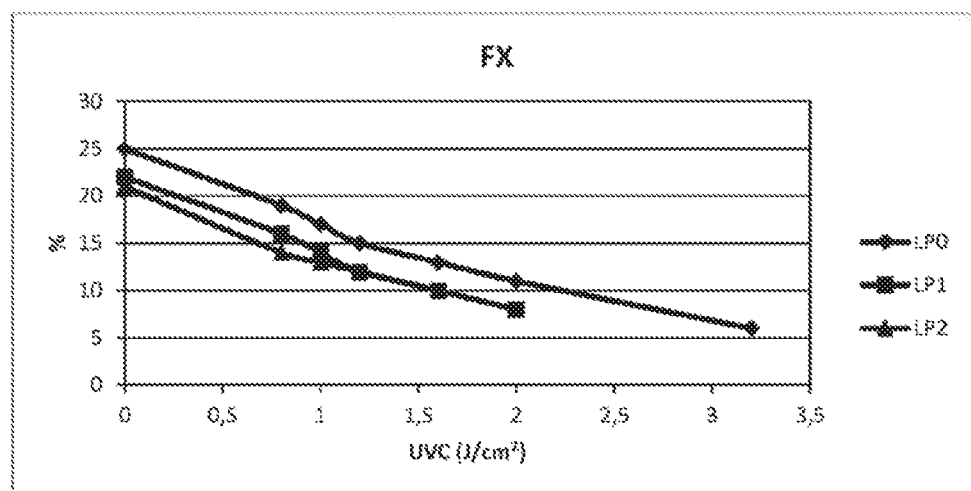
Figure 11:
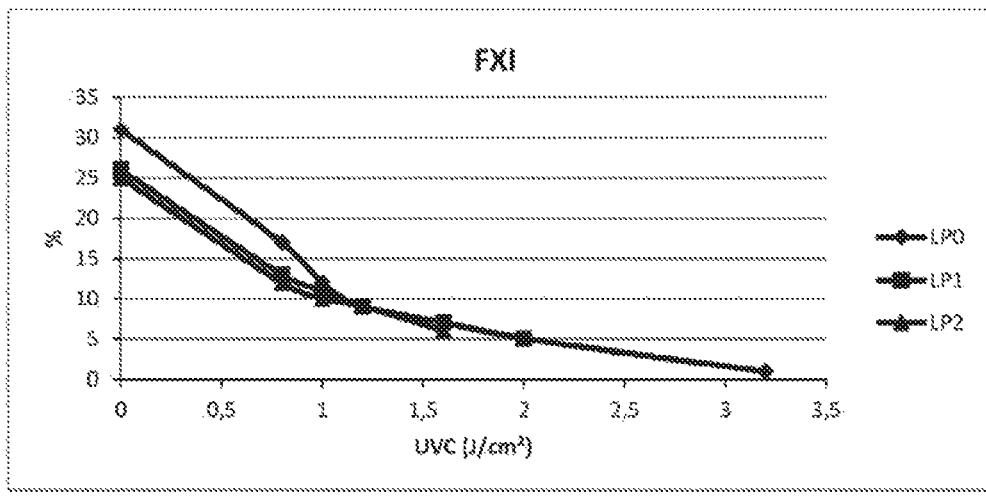

The average of the three batches makes it possible to conclude that the concentration of PDGF-AB is little or not affected by the irradiation with UVC (FIG. 4).

On the other hand, FIGS. 2, 3, 5 and 6 show that the concentration of TGF-beta1, bFGF, EGF and VEGF, decreases as the dose of UVC increases and this, from 0.8 J/cm$^2$.

The losses in EGF and VEGF are not as substantial compared to the losses in bFGF and TGF-beta1. A loss of 23% and 24% respectively is observed for bFGF and TGF-beta1 at 0.8 J/cm$^2$, and up to 50% and 44% respectively at 1.6 J/cm$^2$.

1.4 Dosages of Plasma Factors

Biochemical dosages, carried out on the three same batches, were carried out in order to characterise the platelet lysates irradiated at different UVC doses.

The results of the dosages of the plasma factors in the platelet lysate after irradiation with UVC, shown in FIGS. 7 to 11, show that the UVC have an effect on factors II, VII, IX, X, and XI. As for TGF-beta1, the concentration of these plasma factors decreases according to the UVC dose delivered during the irradiation.

1.5. Impact of the Irradiation with UVC Radiation on the Effectiveness of the PL (Proliferation of MSCs)

Figure 12:
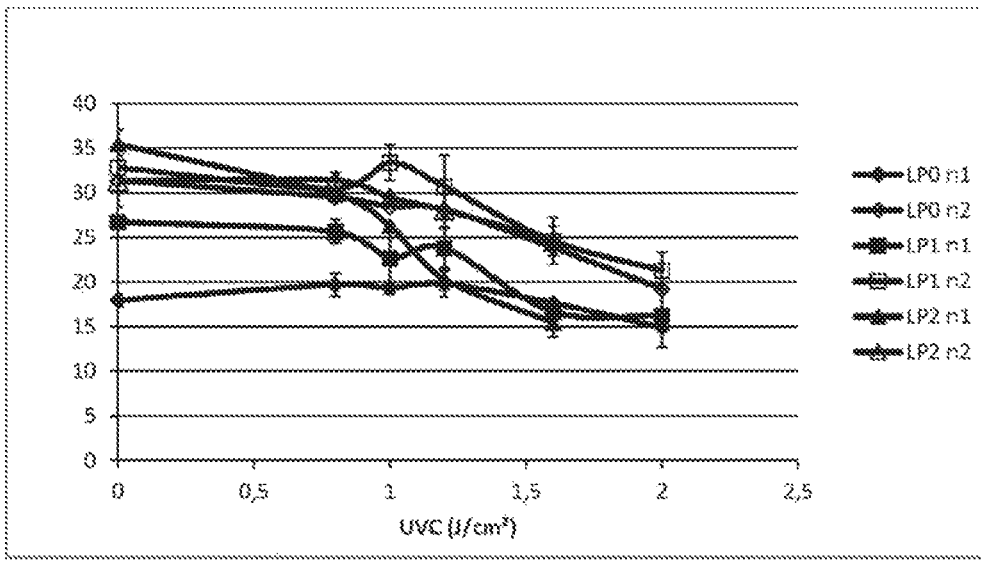
FIG. 12 shows the amplification factors on the 7th day of culture of mesenchymal stem cells cultivated in the presence of platelet lysate irradiated with UVC radiation according to the dose of irradiation.

Proliferation tests, carried out on three batches, were carried out in order to characterise the platelet lysates irradiated at the different doses (FIG. 12).

The mesenchymal stem cells (MSCs) were seeded in 6-well plates (triplicates for each condition) with 2,500 cells/cm$^2$.

All the platelet lysates were used at 8% in an alphaMEM medium. The experiment was carried out twice.

FIG. 12 shows that the two experiments generate the same proliferation profile of the MSCs in contact with the platelet lysate irradiated with UVC radiation.

On the one hand, it can be noted that the controls of non-irradiated platelet lysate are very similar. In addition, a plateau is observed from 0 J/cm$^2$ to 1.2 J/cm$^2$ where the proliferation of the MSCs does not seem to be impacted. Between 1.2 J/cm$^2$ and 1.6 J/cm$^2$ the proliferation of the MSCs starts to visibly decrease.

These experiments have made it possible to determine that an irradiation with UVC radiation at a dose of about 1 J/cm$^2$ made it possible to maintain a concentration of growth factors that is sufficient to ensure good cell proliferation, while still visibly reducing the concentration of coagulation factors.

Example 2

Industrial Production of Platelet Lysate Irradiated with UVC Radiation and with Gamma Radiation 2.1 Preparation of the Platelet Lysate Several batches of platelet lysate (PL) were produced as described in example 1.1 hereinabove, from platelet concentrates comprising platelets suspended in 30% plasma and 70% of an additive solution.

2.2 Irradiation with UVC Radiation

The mixture of platelet lysates is filtered through a filter with a porosity of 0.45 µm before being irradiated with UVC radiation.

The mixture of filtered platelet lysates is transferred, by volume of 500 ml, into irradiation bags. The air and all the bubbles are eliminated from the irradiation bags.

The irradiation bags are then irradiated with a UVC illumination device (Macotronic UV, Maco Pharma), at a dose of 1 J/cm². The irradiation bags are stirred at a speed of 110 rpm.

After irradiation with UVC radiation, the contents of the irradiation bags are re-mixed in a transfer bag and the mixture of the platelet lysates irradiated with UVC radiation is filtered through a sterilising filter with a porosity of 0.2 μm in order to form a batch of platelet lysate irradiated with UVC (PL-UVC).

2.3 Irradiation with Gamma Radiation

The mixture of platelet lysates irradiated with UVC is then redistributed into 50-ml ethylene vinyl acetate bags.

The 50-ml bags are frozen at −80° C. then irradiated with gamma radiation at an absorbed dose of 35 kGy or 55 kGy (PL-UVC-G35 and PL-UVC-G55). The same batch is used for the irradiation at 35 kGy or at 55 kGy.

2.4 Dosage of Cytokines

In samples of PL, PL-UVC-G35 and PL-UVC-G55, the quantity of bFGF (ref.SFB50/lot P116487), PDGF-AB (ref.SHD00C/lot P122623), PDGF-BB (ref.SBB00/lot P116857) and TGF-beta1 (ref.SB100B/lot P119433) is dosed, using commercial Elisa kits.

Figure 13:
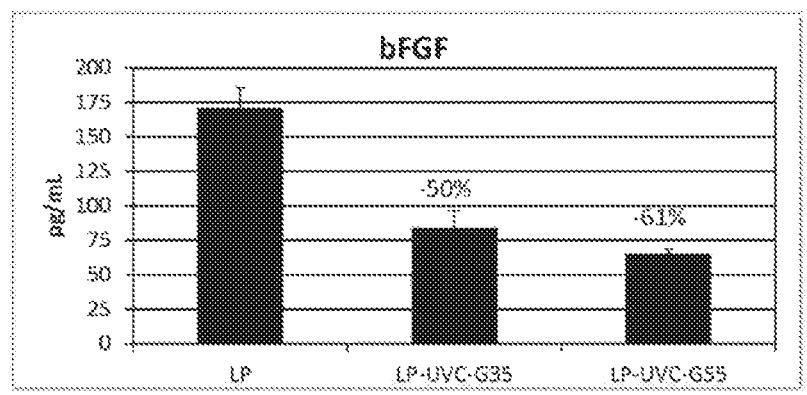
FIGS. 13 to 16, show respectively, the concentrations of bFGF, PDGF-AB, PDGF-BB and TGF-beta1 growth factor, of a non-irradiated platelet lysate (PL), of a platelet lysate irradiated with UVC radiation at a dose of 1 $J/cm^2$ then irradiated with gamma radiation at a dose of 35 kGy (PL-UVC-G35) and of a platelet lysate irradiated with UVC radiation at a dose of 1 $J/cm^2$ then irradiated with gamma radiation at a dose of 55 kGy (PL-UVC-G55).

In FIG. 13, the concentration of bFGF is impacted by the double irradiation with UVC radiation and with gamma radiation. The PL-UVC-G35 loses 50% of its concentration of bFGF and the PL-UVC-G55 loses 61% of its concentration of bFGF. An effect of the dose of the gamma radiation on the losses of bFGF is observed: the higher the dose of irradiation using gamma radiation applied is, the more the loss in bFGF increases.

Figure 14:
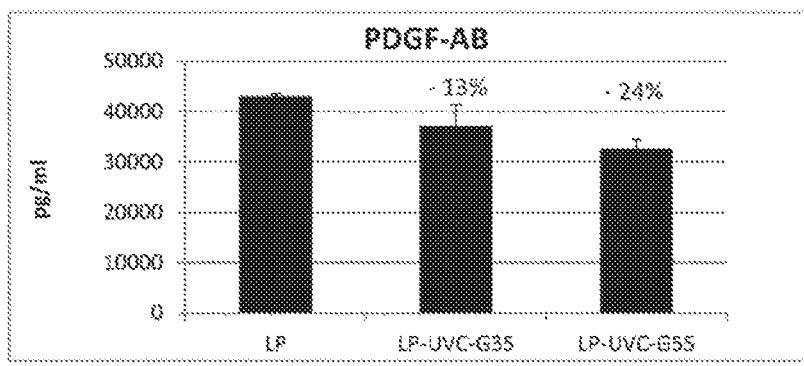

In FIG. 14, the concentration of PDGF-AB is slightly impacted by the double irradiation with UVC radiation and with gamma radiation: the PL-UVC-G35 loses 13% of its concentration of PDGF-AB, the PL-UVC-G55 loses 24% of its concentration of PDGF-AB (FIG. 14).

Figure 15:
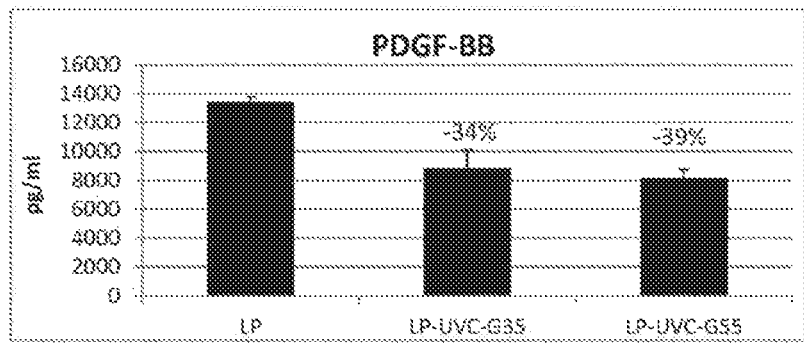

In FIG. 15, the concentration of PDGF-BB is more strongly impacted by the double irradiation with UVC radiation and with gamma radiation than the concentration of PDGF-AB: the PL-UVC G35 kGy loses 34% of its concentration of PDGF-BB, the PL-UVC-G55 loses 39% of its concentration of PDGF-BB. The effect of the dose of the irradiation with gamma radiation on the loss of PDGF-BB is not clearly demonstrated.

Figure 16:
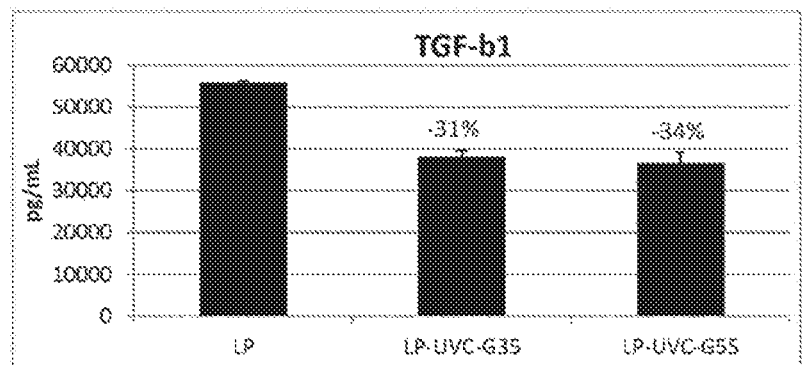

In FIG. 16, the concentration of TGF-beta1 is impacted by the double irradiation with UVC radiation and with gamma radiation, without effect of the dose of gamma radiation: the PL-UVC-G35 loses 31% of its concentration of TGF-beta1, the PL-UVC-G55 loses 34% of its concentration of TGF-beta1.

According to these results, only the concentration of PDGF-AB is slightly impacted by the double irradiation with UVC radiation and with gamma radiation. On the other hand the concentration of bFGF decreases by about 50% for the doses studied.

2.5 Dosage of Proteins

The dosage of proteins is carried out using a BCA kit (UP40840/Q05KL03).

Figure 17:
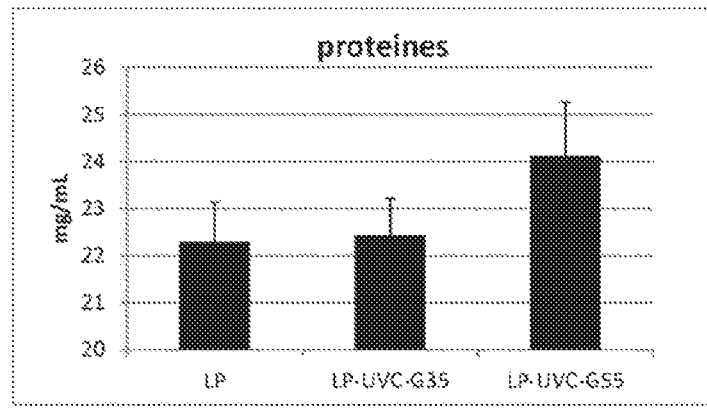
FIGS. 17 and 18 show, respectively, the total protein concentrations and the concentrations of vitamin B12, of a non-irradiated platelet lysate (PL), of a platelet lysate irradiated with UVC radiation at a dose of 1 $J/cm^2$ then irradiated with gamma radiation at a dose of 35 kGy (PL-UVC-G35) and of a platelet lysate irradiated with UVC radiation at a dose of 1 $J/cm^2$ then irradiated with gamma radiation at a dose of 55 kGy (PL-UVC-G55).

No notable effect of a double irradiation with UVC radiation and wth gamma radiation is observed on the concentration of proteins (FIG. 17).

2.6 Biochemical Dosages and Coagulation Factors

Biochemical analyses were carried out on the following 12 elements:

| Biochemical Analyses |
|---|
| Total proteins |
| Serum albumin |
| Calcium |
| Sodium |
| Fibrinogen |
| D-dimers |
| Mycoplasms |
| Vitamin B12 |
| Vitamin D |
| Chlorine |
| Iron |
| Cholesterol |

Figure 18:
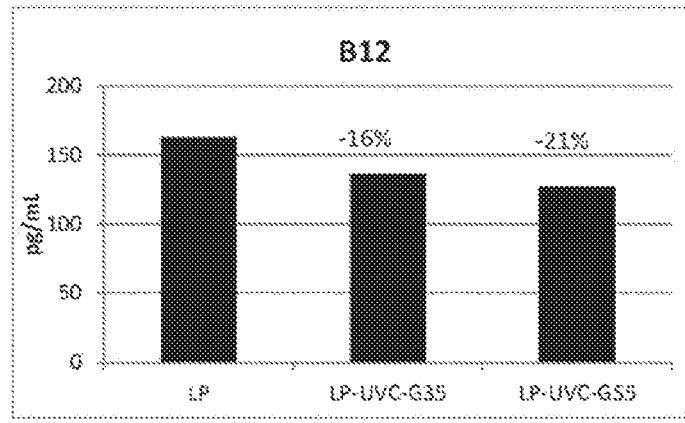

Among the 12 elements dosed, only vitamin B12 is impacted by the double irradiation with UVC radiation and with gamma radiation. The effect of the dose of the irradiation with gamma radiation on the loss of vitamin B12 is not shown (FIG. 18).

According to the table 7 hereinbelow, the concentrations of coagulation factors (FII, FVII, FIX, FX, FXI) and of antithrombin III (ATM), protein involved in coagulation, are impacted by the double irradiation with UVC radiation and with gamma radiation.

An effect of the dose of the irradiation with gamma radiation on the loss of coagulation factors is observed: the stronger the dose of gamma radiation applied is, the more the loss in coagulation factors increases.

TABLE 7

Percentages of difference in concentration of proteins with respect to the starting PL

|  | PL-UVC-G35 | PL-UVC-G55 |
|---|---|---|
| Factor II (FII) | −59.6% | −68.4% |
| Factor VII (FVII) | −50% | −63.6% |
| Factor IX (FIX) | −73.8% | −82.1% |
| Factor (FX) | −66.7% | −75% |
| Factor XI (FXI) | −81.7% | −84.9% |
| antithrombin III | −45.5% | −59.1% |

2.7 Gelation Test

The test was carried out at different concentrations of platelet lysate in the basal medium alphaMEM without heparin: 2.5%, 5%, 8%, 10%, 15%, and 20%.

TABLE 8

| | % PL | | | | | |
|---|---|---|---|---|---|---|
| | 2.5% | 5% | 8% | 10% | 15% | 20% |
| PL | − | + | ++ | +++ | +++ | +++ |
| PL-UVC | − | − | − | + | +++ | +++ |
| PL-G35 | − | − | − | − | ++ | ++ |
| PL-UVC-G35 | − | − | − | − | − | − |
| PL-UVC-G55 | − | − | − | − | − | − |

−: no gelation
+: gelling effect but quasi liquid
++: gelled to 50%
+++: gelled to 100%

For the non-irradiated platelet lysate (PL), with a low percentage of platelet lysate (2.5%), there is no gelling effect. The results show that the more the percentage of platelet lysate present in the basal medium increases, the more substantial the gelation of the basal medium is.

At 5% of PL, the basal medium already has a gelled effect, and at 8% of platelet lysate, the basal medium is gelled to 50%.

The basal medium containing PL-UVC does not begin to gel until concentrations of PL-UVC of 10%, and only at concentrations of PL-G35 of 15%.

At higher percentages (15% and 20%), only the basal mediums containing PL-UVC-G35 and PL-UVC-G55 remain non-gelled.

In conclusion, the basal medium containing doubly irradiated platelet lysate does not gel, and this irrespective of the percentage of this doubly irradiated platelet lysate used (up to strong doses of 20%), even without adding heparin. Thus, the double irradiation substantially degrades the coagulation power of a platelet lysate.

2.8 Proliferation Tests

The cells used are bone-marrow derived primary human mesenchymal stem cells (MSC) coming from two different donors (M065 and M068). Two female experimenters carried out the blind experiment.

The first day, 6-well plates were seeded with 2,500 cells/cm$^2$ in triplicate. The human MSCs are at P3.

The basal medium used is the alphaMEM medium. The platelet lysates are those of table 8, at 8% in the basal medium.

The medium is changed every 3 days. After 7 days of cell culture, the cells are counted with the ViCell.

Figure 19:
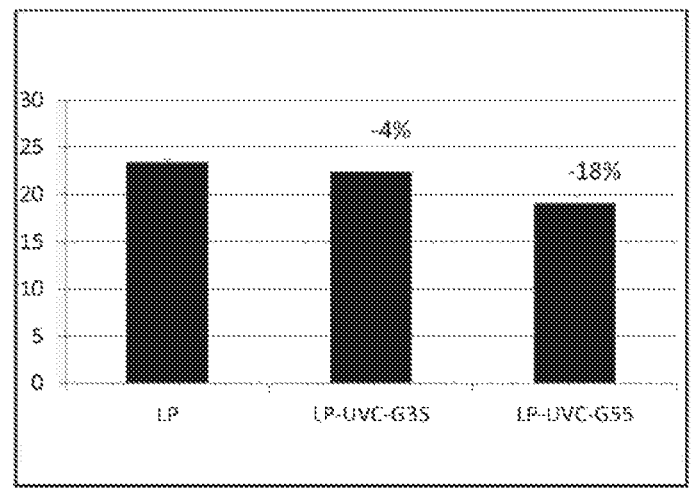
FIG. 19 shows the amplification factors on the 7th day of culture of mesenchymal stem cells cultivated in the presence of a non-irradiated platelet lysate (PL), of a platelet lysate irradiated with UVC radiation at a dose of 1 $J/cm^2$ then irradiated with gamma radiation at a dose of 35 kGy (PL-UVC-G35) and of a platelet lysate irradiated with UVC radiation at a dose of 1 J/cm2 then irradiated with gamma radiation at a dose of 55 kGy (PL-UVC-G55).

Only a low impact of the double irradiation with UVC radiation and with gamma radiation is observed on the effectiveness of the platelet lysate: loss of 4% of the cell proliferation caused by the UVC and gamma radiation at 35 kGy (FIG. 19).

On the other hand, at 55 kGy, the irradiation with gamma radiation has a more marked impact on the effectiveness of the platelet lysate. Thus, the cumulative effect of the irradiation with UVC and with the gamma radiation at 55 kGy generates a loss of 18% in the cell proliferation with respect to the control PL. However, it can be noted that the doubly irradiated PL at 55 kGy remains more effective than the conditions 10% FBS+bFGF at 1 ng/ml (results not shown).

The absence of impact on cell proliferation of the double irradiation of the platelet lysate with UVC and gamma radiation at 35 kGy could be explained by the fact that, on the one hand, the cytokines of interest and, on the other hand, the various biochemical factors important for cell growth (vitamins, etc.), are not impacted or hardly impacted. The relative loss of some of these factors (still present although for some in a lower quantity) could explain the absence of an effect on cell proliferation. In addition, at an irradiation with gamma radiation of 55 kGy, as all of the cytokines are more impacted than at 35 kGy, this would no longer allow for an optimum proliferation of cells, which could explain the negative effect of the double irradiation with UVC and gamma radiation at 55 kGy on cell proliferation (−18%).

What is claimed is:

1. A method for preparing an irradiated platelet lysate comprising the following steps:
    providing a platelet lysate to obtain a starting platelet lysate, the starting platelet lysate comprising platelet factors including growth factors and further comprising plasma proteins including a plurality of coagulation factors and proteins other than the coagulation factors;
    subjecting the starting platelet lysate to double irradiation with UVC radiation having a wavelength between 200 and 280 nm and with ionizing radiation having a wavelength less than or equal to 100 nm to obtain a platelet lysate irradiated with UVC radiation and with ionizing radiation, the double irradiation with UVC radiation and with ionizing radiation being arranged to retain at least 75% of the total protein concentration of the starting platelet lysate while reducing by at least 40% the concentration of at least one of the coagulation factors selected from the group consisting of fibrinogen, factor II, factor VII, factor IX, factor X, and factor XI of the starting platelet lysate.

2. The method according to claim 1, wherein the double irradiation with ionizing radiation and with UVC radiation is arranged to reduce by at least 40% the concentration of each one of the coagulation factors factor II, factor VII, factor IXI, factor X and factor XI of the starting platelet lysate.

3. The method according to claim 1, wherein the irradiation with UVC radiation is arranged to retain at least 75 of the total protein concentration of the starting platelet lysate while reducing by at least 20% the concentration of at least one of the coagulation factors selected from the group consisting of fibrinogen, factor II, factor IX, factor X and factor XI of the starting platelet lysate.

4. The method according to claim 1, wherein the starting platelet lysate comprises TGF-beta1, EGF, PDGF-AB, IGF-1, VEGF and bFGF endogenous growth factors, and the irradiation with UVC radiation is arranged to retain at least 80% of the concentration of at least one of the growth factors selected from the group consisting of IGF-1, PDGF-AB, EGF and VEGF.

5. The method according to claim 1, wherein the irradiation with UVC radiation is carried out at a dose comprised between 0.01 to 2 J/cm$^2$.

6. The method according to claim 1, wherein the starting platelet lysate is irradiated with UVC radiation in a liquid state.

7. The method according to claim 1, further comprising a step of filtering the starting platelet lysate prior to irradiation with UVC radiation through a filter with a porosity of 0.65 μm or less.

8. The method according to claim 1, further comprising a step of sterilising filtration of the platelet lysate after the irradiation irradiated with UVC radiation through a filter with a porosity of 0.45 μm or less.

9. The method according to claim 1, further comprising a step of freezing the platelet lysate prior to the irradiation with the ionizing radiation.

10. The method according to claim 1, wherein the irradiation with ionizing is carried out after the radiation with UVC radiation.

11. The method according to claim 1, wherein the ionizing is a gamma radiation having a wavelength less than or equal to 10 μm.

12. The method according to claim 1, wherein the irradiation with ionizing is carried out at an absorbed dose in the range from 20 kGy to 75 kGy.

13. The method according to claim 3, wherein the irradiation with UVC radiation is arranged to reduce by at least 20% the concentration of each one of the coagulation factors fibrinogen, factor II, factor IX, factor X and factor XI of the starting platelet lysate.

14. The method according to claim 4, wherein the irradiation with UVC radiation is arranged to retain at least 80% of each one of the growth factors IGF-1, PDGF-AB, EGF and VEGF in the starting platelet lysate.

15. The method according to claim 5, wherein the irradiation with UVC radiation is carried out at a dose between between 0.5 J/cm$^2$ and 1.5 J/cm$^2$.

16. The method according to claim 15, wherein the irradiation with UVC radiation is carried out at a dose at 1 J/cm².

17. The method according to claim 7, wherein the step of filtering the starting platelet lysate is through a filter with a porosity of 0.45 μm or less.

18. The method according to claim 8, wherein after the step of sterilising filtration of the platelet lysate after irradiation with UVC radiation is through a filter with a porosity of 0.22 μm or less.

19. The method according to claim 12, wherein the irradiation with ionizing is carried out at an absorbed dose in the range from 35 kGy to 55 kGy.

* * * * *